United States Patent [19]

Young et al.

[11] Patent Number: 4,554,162

[45] Date of Patent: Nov. 19, 1985

[54] CL-1724 ANTIBIOTIC COMPOUNDS, THEIR PRODUCTION AND USE

[75] Inventors: Cynthia A. Young; John P. Schaumberg, both of Ypsilanti; Gerard C. Hokanson; James C. French, both of Ann Arbor; Josefino B. Tunac, Troy, all of Mich.

[73] Assignee: Warner-Lambert Company, Morris Plains, N.J.

[21] Appl. No.: 607,056

[22] Filed: May 4, 1984

[51] Int. Cl.[4] .......................... A61K 35/74; C12P 1/06
[52] U.S. Cl. ..................................... 424/117; 435/169
[58] Field of Search ......................... 424/117; 435/169

Primary Examiner—Jerome D. Goldberg
Attorney, Agent, or Firm—Jerry F. Janssen

[57] ABSTRACT

A strain of actinomycete, NRRL 15758, is capable of producing the CL-1724 complex of compounds under conditions of aerobic fermentation in the presence of assimilable sources of carbon and nitrogen. The compound CL-1724B-2 exhibiting antimicrobial and antitumor activity, is claimed together with pharmaceutical compositions and methods of treating microbial infections and tumors in mammals employing these pharmaceutical compositions.

4 Claims, 6 Drawing Figures

CL-1724 ANTIBIOTIC COMPOUNDS, THEIR PRODUCTION AND USE

BACKGROUND OF THE INVENTION

The present invention relates to pharmaceutical compounds, a purified strain of microorganism capable of producing these compounds, and to pharmaceutical compositions and methods of treatment. More particularly, the present invention relates to the compound CL-1724B-2 produced by fermentation, to a purified strain of actinomycete capable of producing this compound, to pharmaceutical compositions containing the compound, and to a method of treating microbial infections employing these compositions.

SUMMARY AND DETAILED DESCRIPTION

The Microorganism

Figure 1:
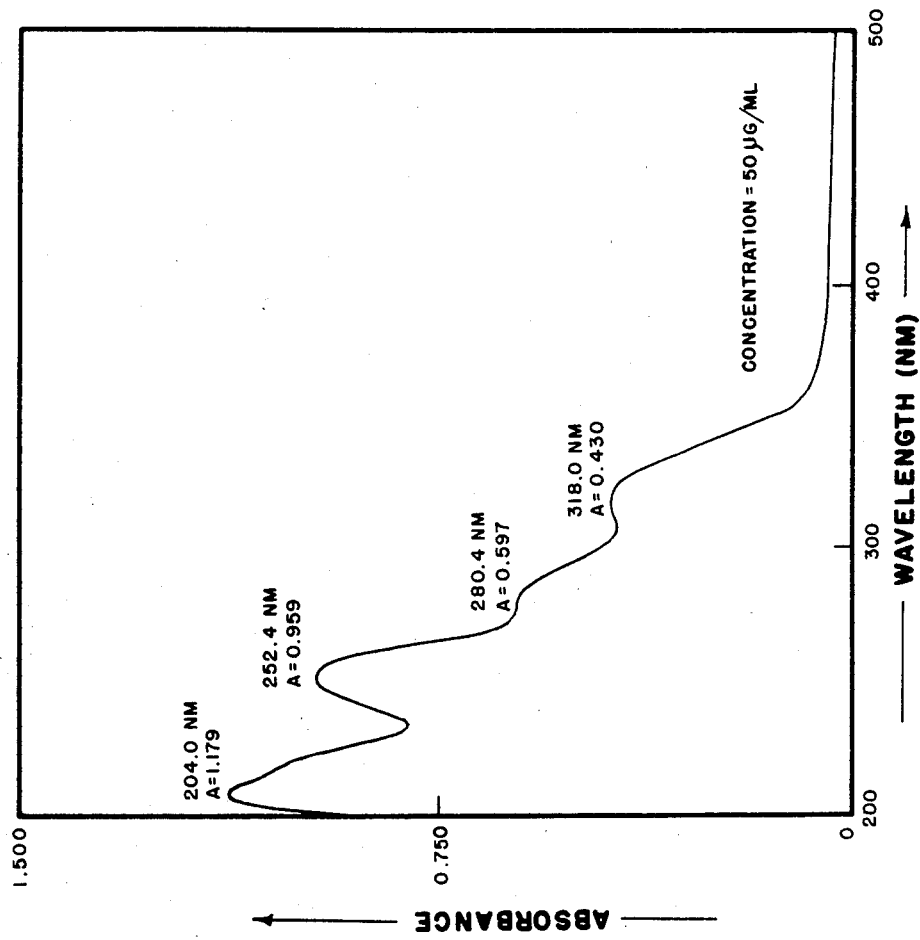
FIG. 1 is the ultraviolet spectrum of CL-1724B-1 compound in methanol.
Figure 2:
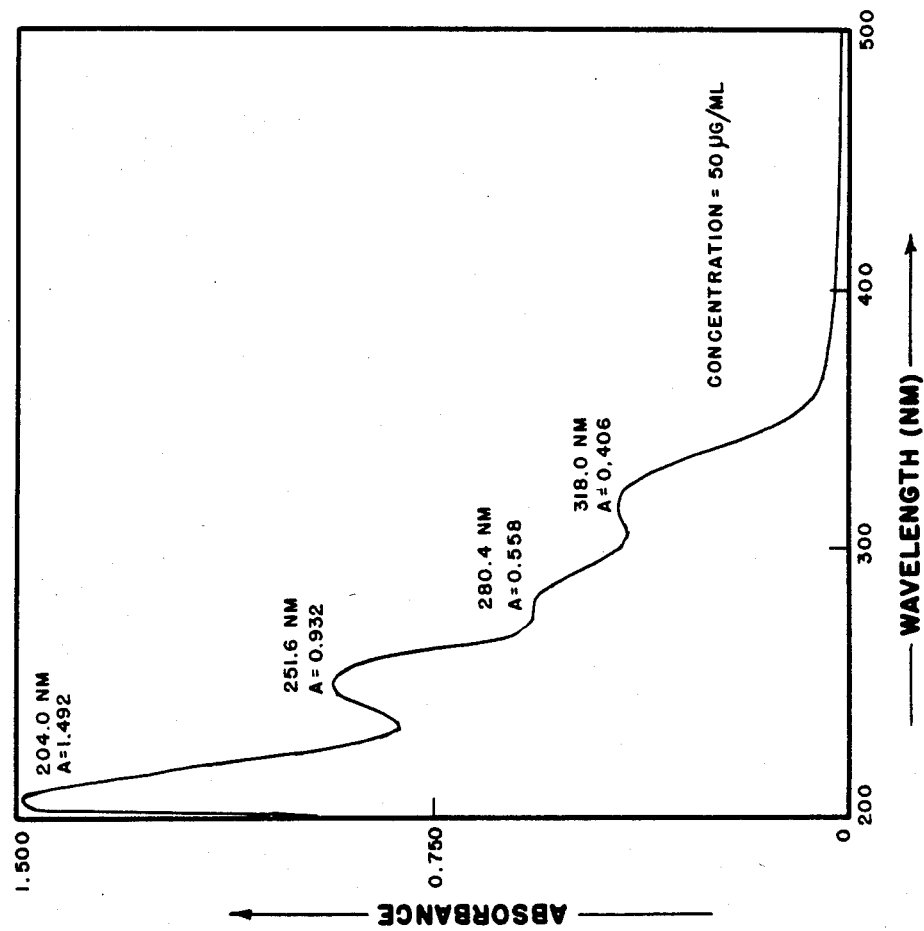
FIG. 2 is the ultraviolet spectrum of CL-1724B-2 compound in methanol.
Figure 3:
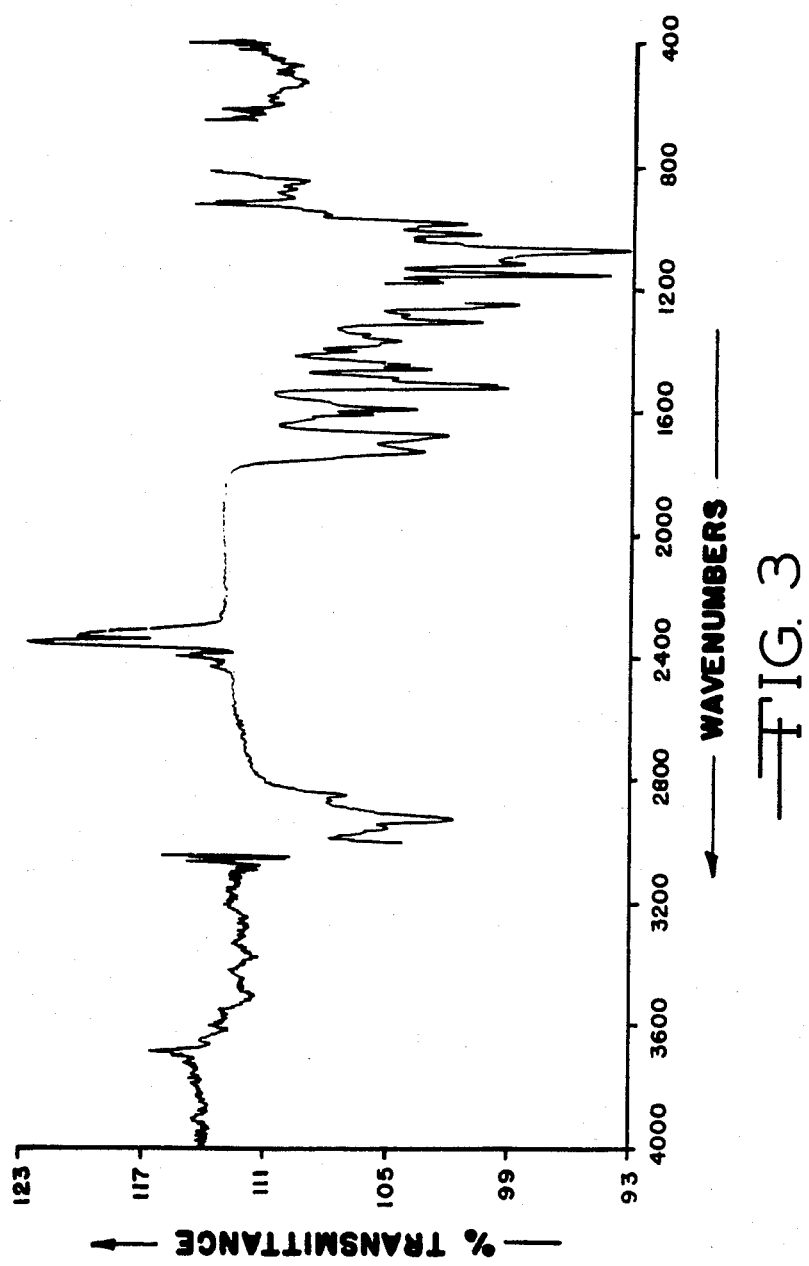
FIG. 3 is the infrared spectrum of CL-1724B-1 compound in chloroform.
Figure 4:
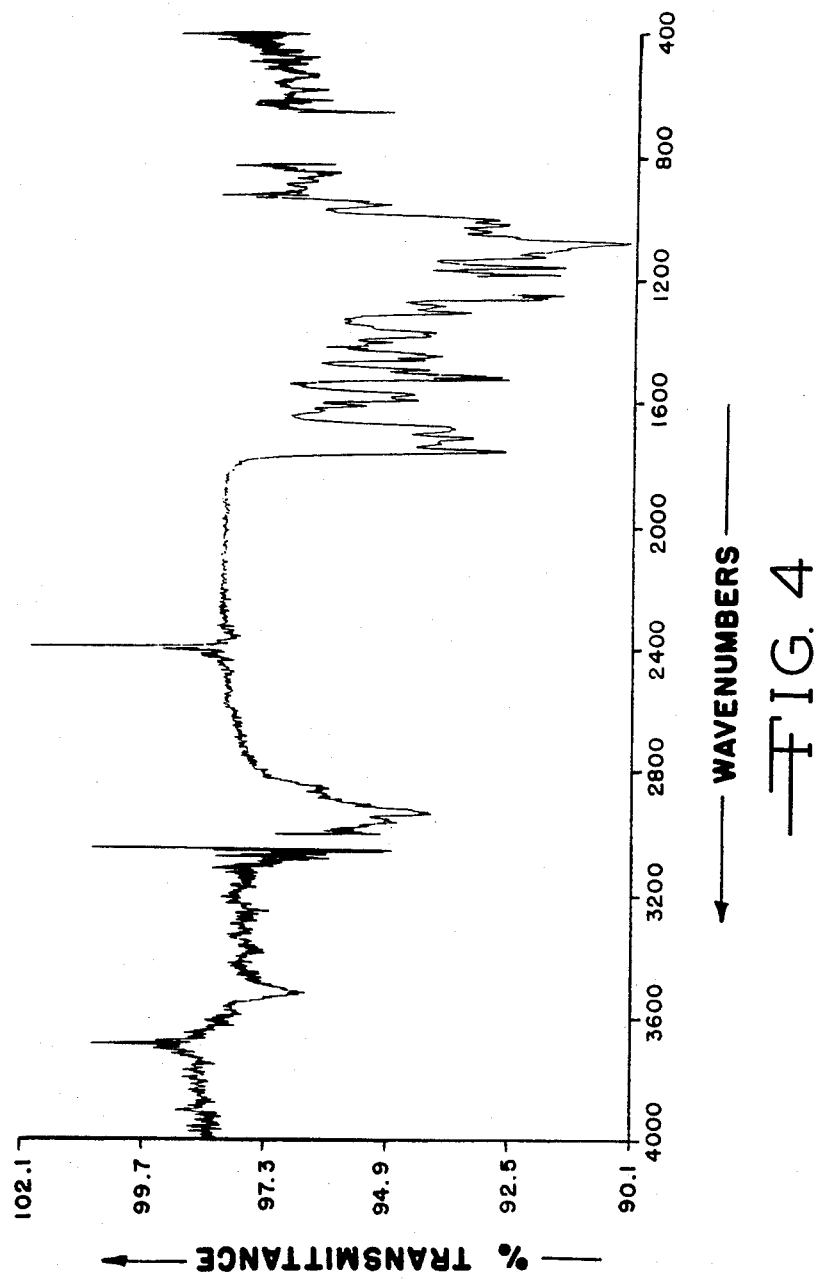
FIG. 4 is the infrared spectrum of CL-1724B-2 compound in chloroform.
Figure 5:
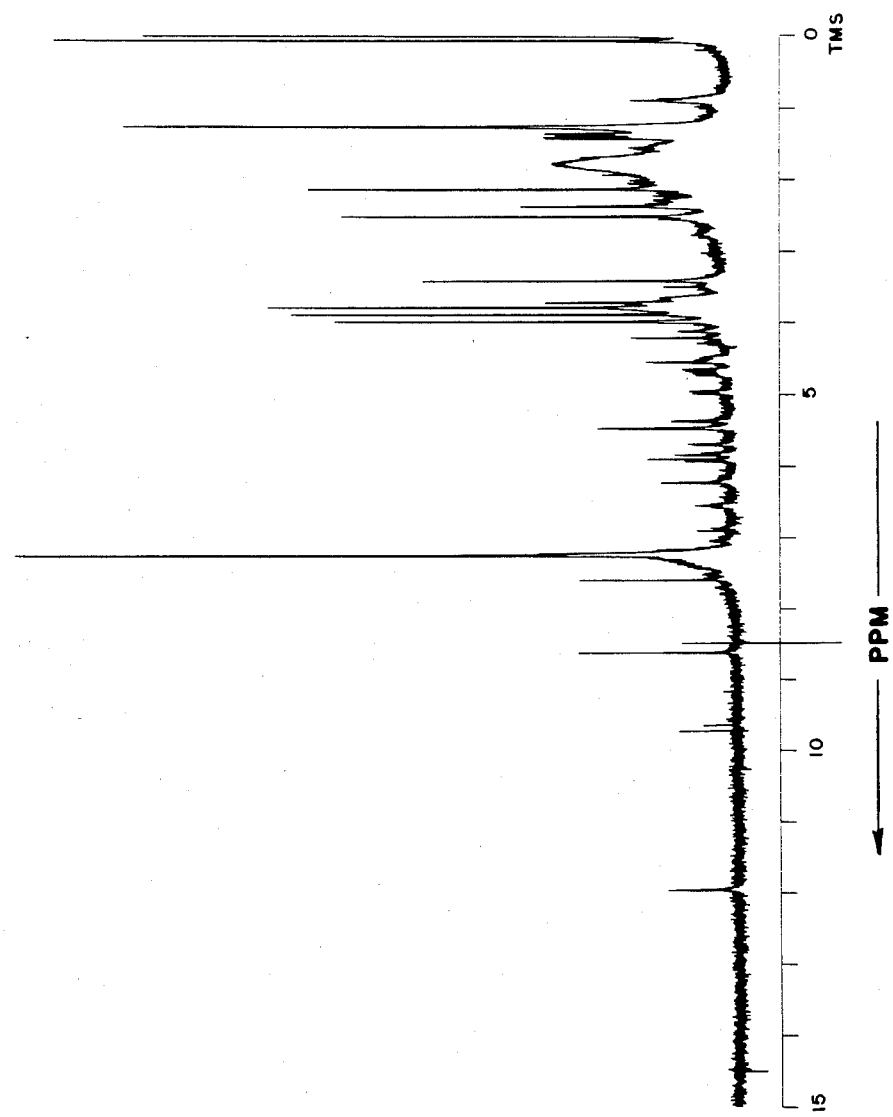
FIG. 5 is the 300 MHz proton magnetic resonance spectrum of CL-1724B-2 compound in deuterochloroform.
Figure 6:
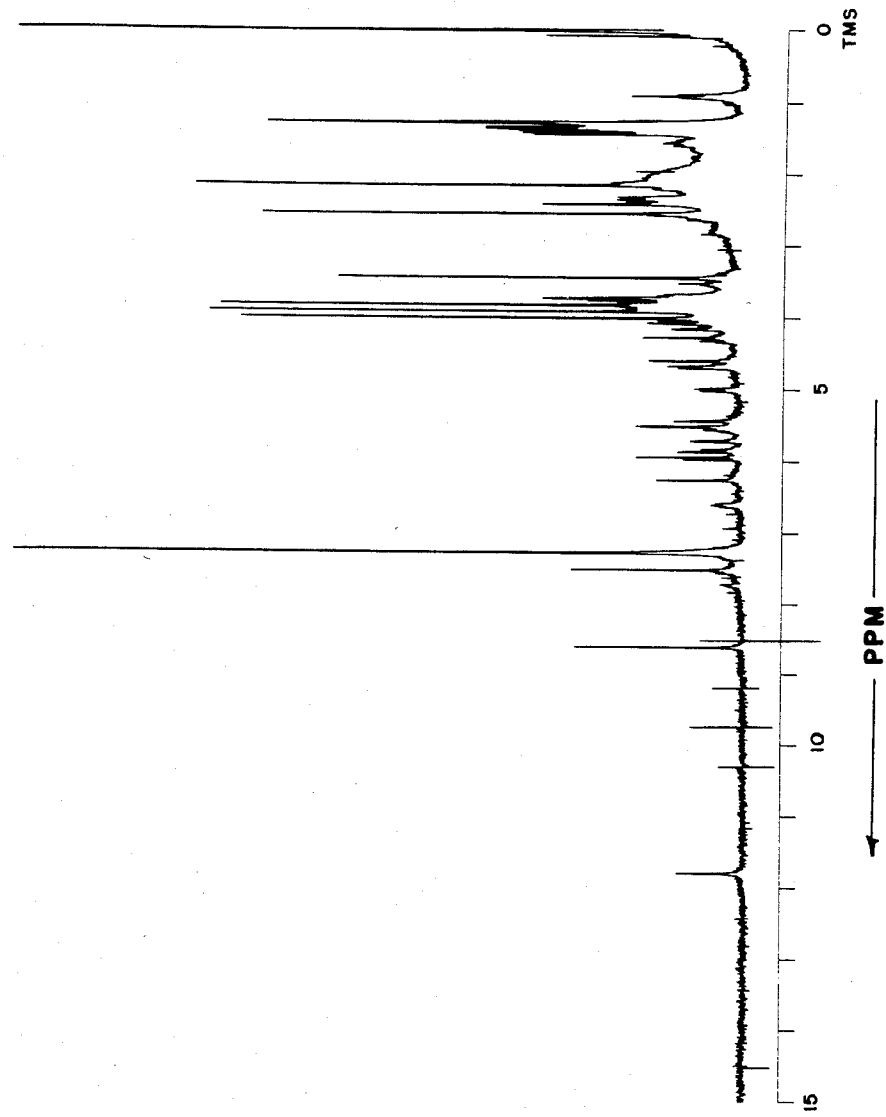
FIG. 6 is the 300 MHz proton magnetic resonance spectrum of CL-1724B-1 compound in deuterochloroform.

In accordance with the present invention, the CL-1724 complex of compounds which possesses antimicrobial activity is produced by cultivating a purified strain of actinomycete, NRRL 15758, under artificial conditions until a sufficient quantity of the CL-1724 complex is formed, and subsequently isolating the individual components.

The actinomycete isolate suitable for the purposes of this invention was found in a soil sample collected in Florida, USA. The microorganism was isolated from the soil sample by standard agar plating techniques using a suitable agar medium containing salts such as potassium dihydrogen phosphate, potassium chloride, magnesium sulfate, ferrous sulfate, and carbon sources such as glycerol and asparagine.

The soil sample was heated in a boiling water bath prior to being plated onto the agar medium and, once plated, was incubated at a favorable temperature, particularly 33° C., to allow for the development of the soil microorganisms.

The CL-1724 complex producing microorganism isolated from the soil sample by the procedure described above is an unidentified actinomycete which has been deposited with the Northern Regional Research Center of the United States Department of Agriculture, 1815 North University Street, Peoria, Ill. 61604, under the terms and conditions of the Budapest Treaty for the Deposit of Microorganisms where it has been given the designation NRRL 15758. This culture of microorganism is also being maintained as a dormant culture in lyophile tubes, cryogenic vials, and in soil sample tubes in the Warner-Lambert/Parke-Davis Culture Collection, 2800 Plymouth Road, Ann Arbor, Mich. 48105, were it bears the designation WP-1234.

Actinomycete NRRL 15758 of the present invention has some characteristics in common with an actinomycete isolate named *Actinomadura pulveraceus*, ATCC 39100, described in European Patent Application No. 0095154 published Nov. 30, 1983. It has been found, however, that the microorganism of the present invention, NRRL 15758, can be differentiated from isolate ATCC 39100 by several important features.

In Table 1 there is shown a comparison of the utilization of carbon sources by NRRL 15758 and ATCC 39100. Utilization of carbon sources by the two microorganisms was determined by the methods detailed in Pridham, T. G. and Gottlieb, D., *J. Bacteriol.*, 56:107–114 (1965).

TABLE 1

Comparison of Carbon Source Utilization of ATCC 39100 and NRRL 15758

| Carbon Source | Utilization* ATCC 39100 | NRRL 15758 |
|---|---|---|
| Glucose | + | + |
| Xylose | + | + |
| Arabinose | − | + |
| Rhamnose | + | + |
| Fructose | − | − |
| Galactose | ± | − |
| Raffinose | − | − |
| Mannitol | − | + |
| Inositol | ± | − |
| Salicin | − | − |
| Sucrose | + | + |

*+ = Utilization
± = Doubtful utilization
− = No detectable utilization

The microorganism of this invention, NRRL 15758, was able to utilize mannitol and arabinose, while ATCC 39100 was not. Additionally, differences between the two microorganisms in the utilization of inositol and galactose were also noted.

As a result of these differences in the metabolic utilization of carbon by the two microorganisms, isolate NRRL 15758 is considered a new species of *Actinomadura*.

The Fermentative Production of the CL-1724 Complex of Compounds

The CL-1724 complex of compounds is produced during aerobic fermentation under controlled conditions by isolate NRRL 15758. The fermentation medium consists of sources of carbon, nitrogen, minerals, and growth factors. Examples of suitable carbon sources are glycerol and various simple sugars such as glucose, mannose, fructose, xylose, ribose, and other carbohydrate-containing materials such as dextrin, starch, cornmeal, and whey. Normally, the quantity of carbon source materials in the fermentation medium varies from about 0.1 to about 10 percent by weight.

Suitable nitrogen sources in the fermentation medium include organic, inorganic, and mixed inorganic-organic nitrogen-containing materials. Examples of such materials are cottonseed meal, soybean meal, corn germ flour, corn steep liquor, distillers dry solubles, peanut meal, peptonized milk, and various ammonium salts.

The addition of minerals and growth factors is also helpful in the production of the CL-1724 complex. Examples of suitable minerals and growth factors include potassium chloride, sodium chloride, ferrous sulfate, calcium carbonate, cobaltous chloride, zinc sulfate, and various yeast and milk products.

The preferred method for producing the CL-1724 complex of compounds is by the submerged culture fermentation method. According to this method, the fermentation medium is prepared by dissolving or suspending the ingredients in water and subsequently sterilizing the resulting medium by autoclaving or by steam heating. The sterilized medium is cooled to a temperature of between 16° C. and 45° C., inoculated with the microorganism, and thereafter fermentation is carried out with aeration and agitation.

In the submerged culture method, fermentation is carried out in shake-flasks or in stationary tank fermentors. In shake-flasks, aeration is achieved by agitating the flasks to bring about intimate mixing of the inoculated medium with air. In stationary tank fermentors, agitation is provided by impellers which may take the form of disc turbines, vaned discs, or open turbine or marine propellers. Aeration is accomplished by sparging air or oxygen into the agitated mixture. Under these conditions, adequate production of the CL-1724 complex is normally achieved after a period of from about two to ten days.

In an alternative embodiment, the CL-1724 complex may also be produced by solid state fermentation of the microorganism.

The following illustrative examples of the fermentative production of the CL-1724 complex of compounds are provided to enable one skilled in the art to carry out the present invention. These examples are not to be read as limiting the present invention as defined by the appended claims, but as merely illustrative thereof.

EXAMPLE 1

Isolation of Actinomycete NRRL 15758

The culture of actinomycete NRRL 15758 of the present invention, following its isolation from a CIM 41 agar plate, by the technique described above, was transferred to an agar slant employing CIM 23 medium and incubated at 33° C. for seven to fourteen days.

TABLE 2

| Formulation of CIM 41 | |
|---|---|
| $K_2HPO_4$ | 1.0 g |
| $MgSO_4.7H_2O$ | 0.5 g |
| KCl | 0.5 g |
| $FeSO_4.7H_2O$ | 0.01 g |
| Glycerol | 30.0 g |
| L-Asparagine | 2.5 g |
| Agar | 15.0 g |
| Distilled Water | 1000.0 ml |

TABLE 3

| Formulation of CIM 23 Medium | |
|---|---|
| Amidex corn starch | 10.0 g |
| N-Z amine, Type A | 2.0 g |
| Beef Extract (Difco) | 1.0 g |
| Yeast Extract (Difco) | 1.0 g |
| $CoCl_2.6H_2O$ | 0.02 mg |
| Agar | 20.0 g |
| Distilled water | 1000.0 ml |

EXAMPLE 2

Shake-Flask Fermentation

A portion of the microbial growth from the agar slant in Example 1 was used to inoculate an 18-mm × 150-mm seed tube containing 5 ml of SD-05 seed medium. The inoculated seed was shaken at 33° C. for three days.

TABLE 4

| Formulation of SD-05 Seed Medium | |
|---|---|
| Yeast extract (Amberex 1003, Amber Labs) | 5.0 g |
| Glucose monohydrate (Cerelose, Corn Products) | 1.0 g |
| Dextrin (Amidex B411, American Maize) | 24.0 g |
| Casein digest (N-Z-case, Sheffield) | 5.0 g |
| Spray dried meat solubles (Jen-Kim) | 3.0 g |
| Calcium carbonate | 2.0 g |
| Deionized water | 1000.0 ml |

A 1-ml portion of the microbial growth from the seed tube was transferred to a 300-ml baffled shake-flask containing 50 ml of SM-41 production medium.

TABLE 5

| Formulation of SM-41 Medium | |
|---|---|
| Sucrose | 15.0 g |
| Dextrin | 10.0 g |
| Cotton seed meal | 6.5 g |
| Peptonized milk | 3.5 g |
| Torula yeast | 2.5 g |
| Deionized water | 1000.0 ml |

The inoculated flask was incubated at 33° C. for four days with shaking (180 rpm gyratory shaker, 5-cm throw). Production of the CL-1724 complex was observed for the first time in this broth.

To confirm the microbial production of the CL-1724 complex, a second 50-ml batch of SM-41 production medium, contained in a 300-ml baffled shake-flask, was inoculated with 2 ml of microbial growth from the seed tube. This mixture was incubated at 33° C. for four days with shaking (180 rpm gyratory shakes, 5-cm throw).

The antitumor activity of both fermentation broths was assayed using L1210 mouse leukemia cells grown in tissue culture. The assay technique is fully described in *Cancer Chemotherapy Reports,* Part 3, Vol. 3, No. 2 (1972), Deran, Greenberg, MacDonald, Schumacher and Abbott. A resulting L1210 leukemia cell growth of 0 to 35% in the presence of the CL-1724 complex was considered active with 0% as most active. The observed activity of the fermentation broths of Example 2, at a dilution of 1:100, is given in Table 6.

TABLE 6

| Antitumor Activity of Fermentation Broths from Example 2 (As Measured Against L1210 Mouse Leukemia Cells) | | |
|---|---|---|
| | % L1210 Cell Growth | |
| Fermentation Stage | Supernate | Freeze-Dried Ethanol Extract |
| a. Shake-flask 1 | 18 | 26 |
| b. Shake-flask 2 | 12 | — |

The crude fermentation broth of shake-flask 2 was also tested for antibacterial activity against various organisms using the agar-disc method. The crude broth was found to be active against *Alcaligenes viscolactis, Bacillus subtilis, Micrococcus luteus, M. lysodeikticus, Branhamella catarrhalis,* and *Staphylococcus aureus.* The antimicrobial activity of the shake-flask 2 fermentation broth as measured by the agar-disc diffusion assay is shown in Table 7.

TABLE 7

Antimicrobial Activity of the Shake-Flask 2 Fermentation Broth

| Microorganism | Culture Number | Zone Diameter (mm) |
|---|---|---|
| Aerobacter aerogenes | 0126 | 0 |
| Alcaligenes faecalis | ATCC 8750 | 0 |
| A. viscolactis | ATCC 21698 | 18.5 |
| Escherichia coli | ATCC 10536 | 0 |
| Bacillus subtilis | 04555 | 16.5 |
| B. subtilis | 04969 | 18.0 |
| B. subtilis | 04969 | 18.5 |
| Micrococcus luteus | 05064 | 20.0 |
| M. lysodeikticus | 04783 | 21.0 |
| Branhamella catarrhalis | 03596 | 28.0 |
| Staphylococcus aureus | 02482 | 17.0 |
| Pseudomonas aeruginosa | NCTC 10490 | 0 |
| Klebsiella pneumoniae | 05037 | 0 |
| Xanthomonas phaseoli | 06002 | 0 |
| Proteus vulgaris | 05062 | 0 |
| Kloeckera africana | 1570 | 0 |
| K. brevis | 1378 | 0 |
| Rhodotorula glutinis | M1384 | 0 |
| Saccharomyces cerevisiae | 01525 | 0 |
| Torulopsis albida | M1390 | 0 |
| Penicillium avellaneum | M2988 | 0 |

EXAMPLE 3

30-Liter Stirred-Jar Fermentation

A cryogenic vial containing approximately 1 ml of a suspension of the culture was used to inoculate 600 ml of SD-05 seed medium contained in a 2-liter baffled shake-flask. The inoculated flask was incubated for about 76 hours at 33° C. on a gyratory shaker at 130 rpm.

After about 76 hours, the contents of the seed flask were transferred aseptically to a 30-liter stainless steel fermentor containing 16 liters of PM-11 production medium. The inoculated medium was incubated at 33° C. for six days while being stirred at 300 rpm and sparged with air at a rate of 1 volume air/volume medium/minute.

The production of the CL-1724 complex was monitored throughout the fermentation cycle by in vitro assay against L1210 mouse leukemia cells and by antimicrobial activity against M. luteus. In addition, such fermentation parameters as pH and percent sedimentation were recorded throughout the fermentation cycle. The data are presented in Table 8.

TABLE 8

Fermentation Profile and Bioactivity of a 30-Liter Fermentation (Example 3)

| Fermentation Time (Hours) | pH | Percent Sediment (Growth) | Zone (mm) vs. M. luteus | L1210, % Growth | | | |
|---|---|---|---|---|---|---|---|
| | | | | 1:500 | 1:2500 | 1:5000 | 1:10000 |
| 0 | 6.8 | — | — | — | — | — | — |
| 24 | 7.3 | 6.0 | 0 | NA* | NA | NA | NA |
| 50 | 7.7 | 7.4 | 18 | 7.5 | 20 | NA | NA |
| 73 | 7.9 | 7.4 | 22 | 0 | 0 | 17.8 | NA |
| 96 | 8.0 | 6.7 | 20 | 0 | 0 | 0 | 27.2 |
| 121 | 8.1 | 9.3 | 20 | 0 | 0 | 0 | 21.3 |
| 144 | 8.1 | 10.7 | 20 | 0 | 0 | 16.8 | 27.6 |

*NA = not active

The harvested beer was also tested for antitumor activity against P388 murine lymphocytic leukemia in vivo by the method detailed in the reference cited above in Example 2. The results of these tests are presented in Table 9.

TABLE 9

Antitumor Activity of Fermentation Broth from Example 3 Against P388 Murine Lymphocytic Leukemia In Vivo

| Dilution of Fermentation Beer | % T/C* | |
|---|---|---|
| | Test 1 | Test 2 |
| undiluted | 123 | 164 |
| 1:2 | 132 | 142 |
| 1:4 | 132 | 136 |
| 1:8 | 126 | 133 |

*% T/C = $\frac{\text{median survival time of treated mice}}{\text{median survival time of control mice}} \times 100$

TABLE 10

Formulation of PM-11

| Lactose | 10.0 g |
|---|---|
| Sucrose | 15.0 g |
| MgSO$_4$.7H$_2$O | 2.5 g |
| CaCO$_3$ | 1.5 g |
| NaCl | 1.0 g |
| Spray dried whey (Krafen) | 5.0 g |
| Defatted corn germ flour | 7.5 g |
| Deionized water | 1000.0 ml |

EXAMPLE 4

200-Gallon Fermentation

Two cryogenic vials, each containing about 1 ml of a suspension of the NRRL 15758 culture, were used to inoculate two 2-liter seed flasks. Each 2-L flask contained 600 ml of SD-05 medium. The inoculated flasks were incubated at 33° C. with shaking on a gyratory shaker, 130 rpm. After 75 hours of incubation, the contents of each seed flasks were used to inoculate two 30-liter stainless steel seed jars. Each seed jar contained 16 liters of SD-05 medium. After inoculation, fermentation was carried out at 33° C. for 24 hours, stirred at 300 rpm, and sparged with air at a rate of 1 volume air/volume medium/minute.

The growing microorganisms from the two seed fermentors were used to inoculate a 200-gallon (757-liter) production fermentor. The production fermentor contained 155 gallons (587 liters) of PM-11 production medium which was steam sterilized for 40 minutes at 121° C. The medium was cooled to 33° C. and then inoculated with about 30 liters of the growing microorganisms from the two seed jars. Fermentation was carried out for four days at 33° C., stirred at 155 rpm, and sparged with air at 0.75 volume air/volume medium/minute. A silicone-based antifoam was used to control foaming as needed.

The bioactivity of the fermentation broth in the 200-gallon fermentor was monitored throughout the fermentation cycle by in vitro assay against L1210 mouse leukemia cells and by antimicrobial activity against M. luteus. The data are presented in Table 11.

TABLE 11

Fermentation Profile and Bioactivity of a 200-Gallon Fermentation (Example 4)

| Fermentation Time (Hours) | pH | Percent Sediment (Growth) | Bioactivity Zone (mm) vs. M. luteus | L1210, % Growth | | | | |
|---|---|---|---|---|---|---|---|---|
| | | | | 1:100 | 1:500 | 1:2500 | 1:5000 | 1:10000 |
| 0  | 7.0 | —   | —    | —    | —  | —    | —    | —  |
| 12 | 6.8 | 4.0 | 0    | —    | —  | —    | —    | —  |
| 24 | 7.1 | 6.7 | 0    | NA*  | NA | NA   | —    | —  |
| 36 | 7.5 | 6.0 | 0    | NA   | NA | NA   | —    | —  |
| 48 | 7.8 | 7.4 | 0    | 13.3 | NA | NA   | —    | —  |
| 60 | 7.7 | 8.0 | 16.0 | 11.5 | NA | NA   | —    | —  |
| 72 | 7.8 | 7.4 | 19.0 | 0    | 0  | 11.5 | NA   | —  |
| 84 | 7.7 | 8.0 | 19.0 | —    | 0  | 0    | 17.0 | NA |
| 96 | 7.8 | 8.0 | 20.0 | —    | 0  | 0    | 11.9 | NA |

*NA = not active

EXAMPLE 5

2000-Gallon Fermentation

A cryogenically preserved sample of isolate NRRL 15758 was thawed and a 1-ml sample was used to inoculate 600 ml of SD-0.5 medium contained in a a 2-liter Erlenmeyer seed flask. The inoculated flask was incubated for 72 hours at 33° C. while being shaken on a gyratory shaker, 130 rpm (5-cm throw).

The resulting microbial growth was used to inoculate 16 liters of SD-05 seed medium in a 30-liter stirred-jar fermentor. THe inoculated jar was incubated for 24 hours while being stirred at 300 rpm and sparged with air at a rate of 1 volume air/volume medium/minute.

The microbial growth from the stirred-jar fermentor was used to inoculate 75 gallons (284 liters) of SD-05 seed medium contained in a 200-gallon (757-liter) fermentor. The medium was sterilized by steam heating at 121° C. for 40 minutes, cooled to 33° C., and then inoculated with about 16 liters of the microbial growth from the stirred-jar. The inoculated 200-gallon fermentor was incubated for 40 hours at 33° C. while being stirred at 155 rpm and sparged with air at a rate of 0.75 volume air/volume medium/minute.

The microbial growth from the 200-gallon seed fermentor was used to inoculate a 2000-gallon (7570-liter) production fermentor. The production fermentor contained about 1300 gallons (4920 liters) of PM-11 production medium which was sterilized by steam heating for 40 minutes at 121° C. After sterilization the fermentor was cooled to 33° C., inoculated with about 75 gallons of microbial growth from the 200-gallon seed fermentor, incubated for 96 hours with stirring at 125 rpm, and sparged with air at a rate of 0.75 volume air/volume medium/minute.

The production of the CL-1724 complex was monitored throughout the fermentation cycle by in vitro assay against L1210 mouse leukemia cells and M. luteus. In addition, fermentation parameters such as pH and percent sedimentation were recorded. The data are presented in Table 12.

TABLE 12

Fermentation Profile and Bioactivity of a 2000-Gallon Fermentor (Example 5)

| Fermentation Time (Hours) | pH | Percent Sediment (Growth) | Bioactivity Zone (mm) vs. M. luteus | L1210, % Growth | | | | |
|---|---|---|---|---|---|---|---|---|
| | | | | 1:100 | 1:500 | 1:2500 | 1:5000 | 1:10000 |
| 0  | 6.9 | —    | —  | —    | —  | —   | —  | —    |
| 12 | 6.9 | 6.0  | —  | —    | —  | —   | —  | —    |
| 24 | 7.2 | 6.7  | 0  | NA*  | NA | NA  | —  | —    |
| 36 | 7.4 | 6.7  | 0  | 12.1 | NA | NA  | —  | —    |
| 48 | 7.7 | 7.4  | 19 | 0    | 0  | 2.5 | —  | —    |
| 60 | 7.8 | 9.3  | 21 | 0    | 0  | 2.2 | —  | —    |
| 72 | 7.7 | 10.0 | 21 | 0    | 0  | 0   | 0  | 8.4  |
| 78 | 7.8 | 9.3  | 21 | 0    | 0  | 0   | 0  | 11.9 |
| 84 | 7.8 | 10.0 | 21 | —    | 0  | 0   | 0  | 7.2  |
| 96 | 7.9 | 9.3  | 20 | —    | 0  | 0   | 0  | 10.6 |

*NA = not active

Chemical Isolation of the CL-1724 Complex

Fermentation beer (625 liters) prepared as described above in Example 4 was adjusted to pH 6.2 with sulfuric acid and mixed for one hour with 568 liters of ethyl acetate. Celite 545 (22.7 kg) was added and the mixture was filtered through a 46-cm plate-and-frame filter press. The filtrate was allowed to stand and the lower aqueous layer which separated was removed. The filter cake was washed with 284 liters of fresh ethyl acetate and the wash was used to extract the separated aqueous layer described above.

After allowing the mixture to separate, the lower aqueous layer was removed. The two ethyl acetate extracts were combined and concentrated to 28.5 liters. After removal of a small amount of inactive precipitated solids, the ethyl acetate extract was further concentrated to 1.6 liters.

The ethyl acetate concentrate was diluted to 16 liters with heptane, and the mixture was extracted twice with 16 liters of with methanol-water (90:10). The lower aqueous methanol layers were combined, washed with 16 liters of heptane, and then concentrated to 8 liters. After further extraction with 8 liters of hexane-chloroform (2:1), the aqueous methanol concentrate (which contained the majority of the CL-1724 complex) was separated and concentrated to 2 liters. Further concentration was effected by adding absolute ethyl alcohol in portions and evaporating to dryness to yield 13.1 g of crude CL-1724 complex.

The crude complex isolated by the methods detailed above was dissolved in methanol and the resulting solution diluted with ethyl acetate. Concentration with addition of ethyl acetate allowed the removal of the methanol to yield two liters of an ethyl acetate soluble fraction and about 1 g of insoluble material which was removed by filtration.

The ethyl acetate-soluble fraction was divided into three portions and each portion was chromatographed separately over silica gel (Prep-PAK-500 (TM), Waters Associates, Milford, Mass., USA). Step gradient elution was effected by employing first, chloroform (2 liters), then chloroform-methanol (96:4, 4 liters), next chloroform-methanol (9:1, 2 liters), and finally chloroform-methanol (8:2, 2 liters). The CL-1724 complex was eluted in the last 3.5 liter portion of the 96:4 chloroform-methanol fractions. Each fraction was analyzed by thin-layer chromatographic assay on silica gel (Baker-flex silica gel, 1B2-F flexible sheets, J. T. Baker, Co., Phillipsburg, N.J., USA) employing 1-butanol-ethyl acetate-n-heptane-ethanol-water (2:8:4:3:1) as a mobile phase. Detection was by bioautography versus *Micrococcus luteus*. Based upon this analysis, fractions were combined and concentrated to dryness to yield residues weighing 1.4 g, 0.6 g, and 0.35 g for fractions A, B, and C, respectively.

Purification of the CL-1724 complex was achieved by further chromatography on silica gel. Thus, a 1.02 g portion of fraction A from above was dissolved in dichloromethane-methanol (99:1) and chromatographed over 75 g of silica gel (Waters Associates, Milford, Mass., USA) contained in a 26 mm×380 mm glass column. Elution was effected with dichloromethane containing increasing amounts of methanol via a step gradient. Each fraction was analyzed by high pressure liquid chromatographic assay and using system b described in Table 13. Fractions richest in the desired materials were combined and concentrated. Elution with dichloromethane-methanol (97.5:2.5) afforded 23.5 mg of semipurified CL-1724B-1, while elution with dichloromethane-methanol (97:3) yielded 25.9 mg of semipurified CL-1724B-2.

Purification and Properties of CL-1724B-1

An 18 mg portion of semipurified CL-1724B-1 from above was dissolved in 1 ml of methanol and chromatographed over 125 g of C-18 silica gel (40 μm particle size, Whatman Chemical Separation, Inc., Clifton, N.J., USA) packed in a 26 mm×460 mm glass column. The silica gel was prepared for chromatography by washing with methanol and then equilibrating with a mobile phase consisting of 0.1M sodium acetate buffer (pH 4.0)-methanol-acetonitrile (40:30:30). After application of the charge, the column was eluted with the same buffer-methanol-acetonitrile solvent system. Several fractions were collected and each was assayed by high pressure liquid chromatography using system a described in Table 13. Fractions containing CL-1724B-1 as the only UV-absorbing peak were combined. The combined eluates (370 ml) were extracted once with 1500 ml of dichloromethane, and then again with 1000 ml of dichloromethane. The combined extracts were washed with 300 ml of water and then concentrated to dryness to yield 5.0 mg of chromatographically pure CL-1724B-1. The properties of CL-1724B-1 are listed in Table 13.

TABLE 13

| Properties of CL-1724B-1 | | |
|---|---|---|
| Ultraviolet absorption in methanol | max | a |
|  | 318 nm | 8.60 |
|  | 280 nm | 11.94 |
|  | 252 nm | 19.18 |
|  | 204 nm | 23.58 |
| Infrared absorption spectrum in chloroform | Principal absorption peaks at 2940, 1735, 1685, 1615, 1600, 1530, 1525, 1465, 1455, 1375, 1315, 1255, 1160, 1080, 1025, 990, 910, 880, and 855 reciprocal centimeters. | |
| 300 MHz proton magnetic resonance spectrum in deuterochloroform | Principal signals at 0.90 (multiplet), 1.25 (singlet), 1.35 (multiplet), 1.50–2.25 (multiplet), 2.35 (multiplet), 2.45–2.90 (multiplet), 3.35–4.20 (multiplet), 4.25 (multiplet), 4.60 (doublet), 4.65 (multiplet), 5.00 (doublet), 5.40 (singlet), 5.50 (multiplet), 5.70 (multiplet), 5.80 (doublet), 5.95 (doublet), 6.25 (singlet), 6.60 (multiplet), 7.50 (singlet), 8.60 (singlet), 12.75 (singlet), all signals measured in parts per million downfield from tetramethylsilane. | |
| High pressure liquid chromatography | | |
| System a: | Column: Partisil 10 ODS-3 C-18 silica gel (Whatman Chemical Separation, Inc., Clifton, New Jersey, USA), 4.6 mm I.D. × 25 cm. Solvent: 0.05 M pH 7.1 ammonium phosphate buffer-acetonitrile (45:55). Flow rate: 2.0 ml/min. Detection: Ultraviolet absorption at 254 nm. Retention time: 8.8 min. | |
| System b: | Column: μ Porasil silica gel (Waters Associates, Inc., Milford, Massachusetts, USA), 3.9 mm I.D. × 30 cm. Solvent: Dichloromethane-methanol (96:4). Flow rate: 1.5 ml/min. Detection: Ultraviolet absorption at 254 nm. Retention time: 4.6 min. | |
| Thin-layer chromatography | | |
| System a: | Solid phase: Bakerflex IB2-F silica gel (J. T. Baker Co., Phillipsburg, New Jersey, USA). Mobile phase: 1-Butanol-ethyl acetate-n-heptane-ethanol-water (2:8:4:3:1). Detection: Bioautography vs. *Micrococcus luteus*. Rf: 0.45 | |
| System b: | Solid phase: Silica gel 60 F-254 (Merck & Co., Rahway, New Jersey, USA). Mobile phase: Chloroform-methanol (92:8). Detection: p-Anisaldehyde spray reagent. Rf: 0.40 | |

Purification and Properties of CL-1724B-2

Semipurified CL-1724B-2 was purified by chromatography over C-18 silica gel (40 μm particle size, Whatman Chemical Separation, Inc., Clifton, N.J., USA) in a manner similar to that described above for CL-1724B-1. Thus, application of a 1 ml solution of semipurified CL-1724B-2 (23 mg) in methanol to the above-described column (previously washed with methanol and equilibrated with the buffered mobile phase), followed by elution with 0.1M sodium acetate buffer (pH 4.0)-methanol-acetonitrile (40:30:30), afforded fractions containing CL-1724B-2 as the only UV-absorbing component as determined by high pressure liquid chromatography assay. These fractions, totaling 630 ml in volume, were combined and extracted once with 2500 ml of dichloromethane and again with 1200 ml of dichloromethane. The combined extracts were washed with 650 ml of water and concentrated to dryness to afford 8.6 mg of chromatographically pure CL-1724B-2. The properties of CL-2724B-2 are listed in Table 14.

TABLE 14
Properties of CL-1724B-2

| | |
|---|---|
| Molecular weight | 1374 Atomic mass units |
| Elemental analysis* | 52.40% C, 6.26% H, 4.08% N, 9.32% S |
| Ultraviolet absorption in methanol | max      a |
| | 318 nm    8.12 |
| | 280 nm    11.16 |
| | 251 nm    18.64 |
| | 204 nm    29.84 |
| Infrared absorption spectrum in chloroform | Principal absorption peaks at 3520, 2940, 1760, 1720, 1685, 1600, 1580, 1520, 1450, 1385, 1375, 1310, 1250, 1155, 1075, 1015, 1000, 955, 900, 875, and 850 reciprocal centimeters. |
| 300 MHz proton magnetic resonance spectrum in deuterochloroform | Principal signals at 0.90 (multiplet), 1.25 (singlet), 1.40 (multiplet), 1.45–2.20 (multiplet), 2.30 (multiplet), 2.40–2.90 (multiplet), 3.30–4.30 (multiplet), 4.50 (multiplet), 4.70 (doublet of doublets), 4.95 (doublet), 5.35 (singlet), 5.45 (doublet), 5.70 (multiplet), 5.80 (doublet), 5.90 (doublet), 6.25 (singlet), 6.55 (multiplet), 7.75 (singlet), 8.65 (singlet), 12.95 (singlet), all signals measured in parts per million downfield from tetramethylsilane. |
| High pressure liquid chromatogrpahy | |
| System a: | Column: Partisil 10 ODS-3 C-18 silica gel (Whatman Chemical Separation, Inc., Clifton, New Jersey, USA), 4.6 mm I.D. × 25 cm. Solvent: 0.05 M pH 7.1 ammonium phosphate buffer-acetonitrile (45:55). Flow rate: 2.0 ml/min. Detection: Ultraviolet absorption at 254 nm. Retention time: 10.0 min. |
| System b: | Column: μ Porasil silica gel (Waters Associates, Inc., Milford, Massachusetts, USA), 3.9 mm I.D. × 30 cm. Solvent: Dichloromethane-methanol (96:4). Flow rate: 1.5 ml/min. Detection: Ultraviolet absorption at 254 nm. Retention time: 5.2 min. |
| Thin-layer chromatography | |
| System a: | Solid phase: Bakerflex IB2-F silica gel (J. T. Baker Co., Phillipsburg, New Jersey, USA). Mobile phase: l-Butanol-ethyl acetate-n-heptane-ethanol-water (2:8:4:3:1). Detection: Bioautoography vs. *Micrococcus luteus.* Rf: 0.45 |
| System b: | Solid phase: Silica gel 60 F-254 (Merck & Co., Rahway, New Jersey, USA). Mobile phase: Chloroform-methanol (92:8). Detection: p-Anisaldehyde spray reagent. Rf: 0.33 |

*By high-resolution mass spectrometry.

Biological Activity of CL-1724B-1 and CL-1724B-2

The biological activity of the compound of this invention against five species of gram-negative bacteria, seven species of gram-positive bacteria, four species of yeast, and two species of fungi was determined using the microtiter dilution technique. This method is described by T. B. Conrath, "Handbook of Microtiter Procedures," Dynatech Corp., Cambridge, Mass., USA (1972); and T. L. Gavan and A. L. Barry, "Microdilution Test Procedures" in *Manual of Clinical Microbiology,* E. H. Lennett ed., American Soc. for Microbiol., Washington, D.C., USA (1980).

Each agent is suspended in a nonaqueous solvent for several minutes to sterilize the compound or, if the compound is completely soluble in water, the aqueous solution is sterilized by passage through a 0.2 to 0.45 micron membrane filter.

Each well of a sterile 96-well microdilution tray is filled under aseptic conditions with 0.1 ml of Mueller-Hinton broth for antibacterial tests, and yeast extract-peptone-dextrose or buffered, supplemented yeast nitrogen base for tests using yeasts or fungi.

A 0.5 ml sample of the test compound solutions is added to each of the eight wells in the first row. A microdilutor apparatus is used to simultaneously mix the contents of these wells and to transfer aliquots to each succeeding row of cells to obtain a range of serially diluted solutions, e.g., concentrations of 1000, 333, 111, 37, 12.3, 4.1, 1.37, and 0.46 micrograms/ml. The last row of wells is untreated and serves as a control.

Each well containing broth and test compound is inoculated with about ten microliters of inoculum of the test microorganism. One well in the last row of wells (which are free of test compound) is not inoculated to provide a sterility control. The trays are sealed and incubated. Media inoculated with bacteria are incubated at 37° C. for 16-24 hours, while those containing yeasts or fungi are incubated at 28° C. for 36-48 hours. During incubation, the inoculated medium is shaken at 100-140 rpm to increase contact between the cells and test compounds.

After the incubation period, each plate is placed on a test reading mirror and the inhibition end points are observed and recorded. The lowest concentration of test compound producing inhibition of the growth of the microorganism (MIC value) is used as the measure of the activity of the test compound. MIC values of <0.5 μg/ml to 333 μg/ml are considered indicative of activity; MIC values of 333 μg/ml to 1000 μg/ml are considered indicative of marginal activity; and MIC values of >1000 μg/ml are considered indicative of inactivity of the test compound against the given microorganism.

The antimicrobial activities of CL-1724B-1 and CL-1724B-2 appear in Tables 15 and 16, respectively.

TABLE 15

Antimicrobial Activity of CL-1724B-1

| Microorganism | Minimal Inhibitory Concentration (μg/ml) | Rating |
|---|---|---|
| Escherichia coli | 0.06 | Active |
| Salmonella typhimurium | <0.02 | Active |
| Alcaligenes viscolactis | <0.02 | Active |
| Branhamella catarrhalis | <0.02 | Active |
| Pseudomonas aeruginosa | 0.5 | Active |
| Micrococcus luteus | <0.02 | Active |
| Staphylococcus aureus | <0.02 | Active |
| Streptococcus pyogenes | <0.02 | Active |
| Streptococcus pneumoniae | <0.02 | Active |
| Streptococcus faecalis | <0.02 | Active |
| Bacillus cereus | <0.02 | Active |
| Bacillus megaterium | <0.02 | Active |
| Saccharomyces cerevisiae | <0.02 | Active |
| Torulopsis albida | <0.02 | Active |
| Mucor paraciticus | 0.5 | Active |
| Rhizopus japonicus | 0.5 | Active |

TABLE 16

Antimicrobial Activity of CL-1724B-2

| Microorganism | Minimal Inhibitory Concentration (μg/ml) | Rating |
|---|---|---|
| Escherichia coli | 0.05 | Active |
| Salmonella typhimurium | <0.02 | Active |
| Alcaligenes viscolactis | <0.02 | Active |
| Branhamella catarrhalis | <0.02 | Active |
| Pseudomonas aeruginosa | 1.5 | Active |
| Micrococcus luteus | <0.02 | Active |
| Staphylococcus aureus | <0.02 | Active |
| Streptococcus pyogenes | <0.02 | Active |
| Streptococcus pneumoniae | <0.02 | Active |
| Streptococcus faecalis | <0.02 | Active |
| Bacillus cereus | <0.02 | Active |
| Bacillus megaterium | <0.02 | Active |
| Saccharomyces cerevisiae | 0.17 | Active |
| Torulopsis albida | 0.17 | Active |
| Mucor paraciticus | 4.6 | Active |
| Rhizopus japonicus | 14 | Active |

The data appearing in Tables 15 and 16 indicate that CL-1724B-1 and CL-1724B-2 possess considerable activity as agents against a wide range of gram-negative and gram-positive bacteria, and fungi.

Cytotoxic Activity of CL-1724B-1 and CL-1724B-2 Against L1210 Murine Leukemia Cells in Vitro The cytotoxic antitumor activity of CL-1724B-1 and CL-1724B-2 against L1210 murine leukemia cells in vitro was determined using the method detailed in R. I. Geran, et al., "Protocols for Screening Chemical Agents and Natural Products Against Animal Tumors and Other Biological System," 3rd Edition, Cancer Chemotherapy Reports, Part 3, Vol. 3, 1–87 (1972) which is incorporated herein by reference. The data from these tests appear in Table 17.

TABLE 17

Cytotoxic Activity of CL-1724B-1 and CL-1724B-2 Against L1210 Murine Leukemia Cells in Vitro

| Compound | $ID_{50}$ (μg/ml) |
|---|---|
| CL-1724B-1 | $1.18 \times 10^{-4}$ |
| CL-1724B-2 | $2.1 \times 10^{-4}$ |

The in vivo antitumor activities of CL-1724B-1 and CL-1724B-2 against P388 murine leukemia were tested in accordance with the protocol in Geran, et al. cited above. The mice were infected intraperitoneally on Day 0 and then administered appropriate doses of CL-1724B-1 or CL-1724B-2 on Days 1–9. The percent median survial times of treated mice compared to untreated mice (%T/C values) appear in Table 18.

TABLE 18

In Vivo Activity of CL-1724B-1 and CL-1724B-2 Against P388 Leukemia in Mice

| Compound | Dosage (mg/kg/inj) | % T/C* |
|---|---|---|
| CL-1724B-1 | 0.020 | toxic |
| | 0.010 | toxic |
| | 0.005 | 93 |
| | 0.0025 | 143 |
| | 0.00125 | 127 |
| CL-1724B-2 | 0.020 | 140 |
| | 0.010 | 134 |
| | 0.005 | 125 |
| | 0.0025 | 107 |

*% T/C = $\frac{\text{median survival time of treated mice}}{\text{median survival time of control mice}} \times 100$ The compounds of the present invention are useful for their antimicrobial activity as pharmaceutical compositions in combination with a compatible pharmaceutically acceptable carrier. These compositions may also contain other antimicrobial agents. The compositions may be made up in any pharmaceutically appropriate form for the desired route of administration. Examples of such forms include solid forms for oral administration as tablets, capsules, pills, powders and granules, liquid forms for topical or oral administration as solutions, suspensions, syrups, and elixirs, and forms suitable for parenteral administration such as sterile solutions, suspensions, or emulsions.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders, or tablet disintegrating agents; it can also be encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 0.1 to 1.0 to about 70 percent of the active ingredient. Suitable solid carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby to solidify.

Liquid form preparations include solutions, suspensions, and emulsions. As an example may be mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerine, propylene glycol, and the like as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

The quantity of active compound in a unit dose of preparation may be varied or adjusted from 0.01 mg to 50 mg preferably to from 0.5 to 10 mg according to the particular application and the potency of the active ingredient. The compositions can, if desired, also contain other compatible therapeutic agents.

In therapeutic use, the mammalian dosage range for a 70 kg subject is from 0.1 to 150 mg/kg of body weight per day or preferably 0.2 to 75 mg/kg of body weight per day. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired.

We claim:

1. The compound designated CL-1724B-2 possessing antimicrobial activity; compound CL-1724B-2 characterized by:

a molecular weight of 1374 atomic mass units; an elemental analysis corresponding to 52.4% C, 6.26% H, 4.08% N, 9.32% S, 27.94% O;

an ultraviolet absorption spectrum in methanol showing absorption maxima at 318 nm (a=8.12), 280 nm (a=11.16), 251 nm (a=18.64), and 204 nm (a=29.84);

an infrared absorption peaks at 3520, 2940, 1760, 1720, 1685, 1600, 1580, 1520, 1450, 1385, 1375, 1310, 1250, 1155, 1075, 1015, 1000, 955, 900, 875, and 850 reciprocal centimeters; a 300 MHz proton magnetic resonance spectrum in deuterochloroform exhibiting principal signals at 0.90 (multiplet), 1.25 (singlet), 1.40 (multiplet), 1.45–2.20 (multiplet), 2.30 (multiplet), 2.40–2.90 (multiplet), 3.30–4.30 (multiplet), 4.50 (multiplet), 4.70 (doublet of doublets), 4.95 (doublet), 5.35 (singlet), 5.45 (doublet), 5.70 (multiplet), 5.80 (doublet), 5.90 (doublet), 6.25 (singlet), 6.55 (multiplet), 7.75 (singlet), 8.65 (singlet), 12.95 (singlet), all signals measured in parts per million downfield from tetramethylsilane.

2. A pharmaceutical composition comprising an antimicrobially effective amount of CL-1724B-2 compound as defined in claim 1 in combination with a pharmaceutically acceptable carrier.

3. A process for the production of CL-1724B-2 compound as defined in claim 1 which comprises cultivating a strain of actinomycete NRRL 15758 under aerobic conditions in a culture medium containing assimilable sources of carbon and nitrogen until a substantial amount of CL-1724B-2 compound is produced and subsequently isolating said compound.

4. A method of treating microbial infections in a mammal comprising administering to a mammal in need of such treatment an antimicrobially effective amount of compound CL-1724B-2 as defined in claim 1 in combination with a pharmaceutically acceptable carrier.

* * * * *